United States Patent [19]
Dandekar et al.

[11] Patent Number: 5,811,630
[45] Date of Patent: Sep. 22, 1998

[54] PSA PROCESS WITH REACTION FOR REVERSIBLE REACTIONS

[75] Inventors: Hemant W. Dandekar, Chicago; Gregory A. Funk, Carol Stream, both of Ill.

[73] Assignee: UOP LLC, Des Plaines, Ill.

[21] Appl. No.: 638,705

[22] Filed: Apr. 29, 1996

Related U.S. Application Data

[63] Continuation-in-part of Ser. No. 330,780, Oct. 28, 1994, Pat. No. 5,523,326.

[51] Int. Cl.$^6$ .............................. C07C 5/22; C07C 7/12; C07C 9/14; B01D 53/047

[52] U.S. Cl. ......................... 585/738; 585/739; 585/748; 585/750; 585/751; 95/97; 95/98; 95/99; 208/346

[58] Field of Search .................................... 585/738, 739, 585/741, 744, 747, 748, 750, 751, 315, 820, 830; 208/310 Z, 346; 95/97, 98, 99

[56] References Cited

U.S. PATENT DOCUMENTS

| | | | |
|---|---|---|---|
| 3,176,444 | 4/1965 | Kiyonaga | 55/26 |
| 3,430,418 | 3/1969 | Wagner | 55/26 |
| 3,703,068 | 11/1972 | Wagner | 55/21 |
| 3,986,849 | 10/1976 | Fuderer et al. | 55/25 |
| 4,210,771 | 7/1980 | Holcombe | 585/701 |
| 4,731,387 | 3/1988 | Westerterp | 518/706 |
| 4,968,722 | 11/1990 | Westerterp | 518/706 |
| 5,254,368 | 10/1993 | Kadlec et al. | 423/247 |
| 5,348,707 | 9/1994 | Harandi et al. | 422/129 |

FOREIGN PATENT DOCUMENTS 2233329  1/1991  United Kingdom .

OTHER PUBLICATIONS

Alpay E., et al. "Combined Reaction and Separation in Pressure Swing Processes" presented at the International Symposium on Chemical Reaction Engineering, Baltimore, Maryland, Sep. 25–28, 1994.

Kirby, N.F. and Morgan, J.E.P., "A Theorectical Investigation of Pressure Swing Reaction," *Transactions of Industrial Chemical Engineering*, vol. 72, Part A, Jul. 1994, pp. 541–550.

Primary Examiner—Bekir L. Yildirim
Attorney, Agent, or Firm—Thomas K. McBride; John G. Tolomei; Richard P. Silverman

[57] ABSTRACT

A process is disclosed for the production of a high octane product from a feed mixture comprising $C_5$–$C_6$ normal paraffins in which an equilibrium reaction to produce mono and dimethyl branched paraffins is achieved by conducting the reaction and the product separation in a pressure swing adsorption and reaction zone containing a uniformly distributed adsorbent for the selective adsorption of normal paraffins and a catalyst for the equilibrium conversion of normal paraffins to mono and dimethyl branched paraffins. More specifically, the process achieves the isomerization of the normal paraffins by the reaction of the normal paraffins in the presence of hydrogen with the simultaneous removal of the mono and dimethyl branched paraffin product at the same temperature and pressure. In one embodiment, the passing of the feed mixture to the bed is terminated and the bed is purged with one of the reactants which in turn further reacts to displace heavier paraffin and enhance the overall product octane. The advantage of the present invention over the conventional process is the higher octane of the product produced and that this higher octane can be achieved at lower severity since the product is removed from the reaction zone as soon as it is produced. The lower operating severity provides longer catalyst life, and reduces the amount of heavy paraffins lost to side reactions such as cracking.

18 Claims, 3 Drawing Sheets

PSA PROCESS WITH REACTION FOR REVERSIBLE REACTIONS

CROSS-REFERENCE

This application is a continuation-in-part of U.S. application Ser. No. 08/330,780, filed Oct. 28, 1994, and issued on Jun. 4, 1996 as U.S. Pat. No. 5,523,326, hereby incorporated by reference.

FIELD OF THE INVENTION

This invention pertains to the field of chemical reaction combined with adsorptive separation. More particularly, the invention relates to the combination of pressure swing adsorption processes with reversible chemical reactions. Most particularly this invention relates to the field of isomerization of paraffins by a combination of a pressure swing adsorption process and reaction for the production of high octane gasoline components.

BACKGROUND OF THE INVENTION

Theoretical models of adsorptive reactors which combine multi-bed pressure swing adsorption and chemical reaction have been studied for some limited types of reversible and irreversible reactions. A paper entitled, "Combined Reaction and Separation in Pressure Swing Processes," by E. Alpay et al. and presented at the International Symposium on Chemical Reaction Engineering, Sep. 25–28, 1994, Baltimore, Md., describes the advantages of such a system for a dissociation reaction producing two components where one of the products is the only adsorbing component. Another paper entitled, "A Theoretical Investigation of Pressure Swing Reaction," by N. F. Kirkby and J.E.P. Morgan, and published in the *TRANSACTIONS OF INDUSTRIAL CHEMICAL ENGINEERING*, Vol. 72, Part A, July 1994, explores a simplified model of pressure swing reaction applied to a non-adsorbable reactant undergoing an irreversible reaction to produce an adsorbable product. These studies indicate that combinations of pressure swing adsorption and reaction have some advantages over conventional reaction systems. The conclusions reached by these studies suggest that the results of the combined PSA and reaction, process are significantly different from conventional PSA technology and the steps of the cyclic operation are dependent upon the many variables that relate to the relative adsorption of the products and reactants and the degree to which equilibrium reactions are affected by the adsorption of the reactants and the products of the reaction. To date there have been few commercial applications of combined pressure swing adsorption and reaction where the reactants and the products can be non-adsorbable, less-readily adsorbable and more-readily adsorbable.

U.S. Pat. No. 4,968,722 to Westerterp discloses a process for producing methanol by reacting carbon monoxide and hydrogen wherein these reactants in the gas phase are introduced into a reaction zone comprising one or more fixed catalyst beds and a liquid absorbent. The liquid absorbent selectively absorbs substantially all of the methanol produced. The liquid absorbent is subsequently pumped out of the reactor and flashed to recover the product methanol. In an earlier patent, U.S. Pat. No. 4,731,387, Westerterp discloses a methanol reaction zone containing a fixed bed of coarse catalyst particles having interstices between them and passing a fine particle solid adsorbent downwardly through the interstices to adsorb substantially all of the methanol product. U.S. Pat. No. 5,254,368 to Kadlec et al. discloses the integral coupling of reaction with a single-bed rapid cycle pressure swing adsorber to provide better separation and more efficient, irreversible reactions wherein the reactant is adsorbed, and those wherein the reactant is not adsorbed. Kadlec et al. describe the use of a single-bed pressure-periodic process for a two-reactant CO oxidation process for automobile pollution control. Kadlec et al. further teach a sequence of operation of the single-bed process which includes a delay step following the introduction of the feed gas and prior to an exhaust step, such that during the delay step the pressure within the single-bed adsorber is permitted to equalize as a continuous stream of product is removed.

Alkane isomerization processes are widely used by refiners to convert normal $C_4$ and $C_5$ alkanes and normal and mono-methyl-branched $C_6$ alkanes into more valuable branched akanes. The multi-methyl-branched $C_6$ alkanes have a higher octane number and are used as gasoline blending components to boost the octane number of the gasoline. The mono-methyl-branched $C_4$ and $C_5$ alkanes may also be used as intermediates, after dehydrogenation, for such oxygenate products as methyl tertiary butyl ether, ethyl tertiary butyl ether, and tertiary amyl methyl ether.

Typically, commercial isomerization processes have had at least a two-stage design; the first stage is a fixed bed reactor, and the second stage is a separation unit. See, for example, U.S. Pat. Nos. 5,146,037 and 5,245,102. The isomerization that takes place in the fixed bed reactor is limited by thermodynamic equilibrium, which results in the reactor effluent containing a substantial amount of unconverted alkanes. The separation unit, which is usual either an adsorption or a fractionation unit, is used to separate the unconverted alkanes from the isomerized product alkanes. The unconverted alkanes are generally recycled to the fixed bed reactor. With this type of design, the recycle stream is usually substantial, and methods of increasing the yield of highly branched alkanes are in demand. One commercial process for the isomerization of C5/C6 paraffins is disclosed in U.S. Pat. No. 4,210,771, hereby incorporated by reference, which integrates pressure swing adsorption with a separate fixed bed isomerization reactor.

U.S. Pat. No. 4,783,574 disclosed a fixed bed reactor containing two sub-beds of adsorbent at opposite ends of the reactor and one sub-bed of catalyst in the center of the reactor. The feed was introduced near the catalyst sub-bed, and a desorbent was introduced at one end of the reactor. The isomerization was catalyzed and unconsumed reactants were adsorbed on the adsorbent sub-bed downstream of the catalyst sub-bed in the direction of the desorbent flow. Then the desorbent flow was reversed by introducing the desorbent from the opposite end of the reactor to desorb the unconsumed reactants and carry them back to the catalyst sub-bed.

Pressure swing adsorption (PSA) provides an efficient and economical means for separating a multi-component gas stream containing at least two gases having different adsorption characteristics. The more strongly adsorbable gas can be an impurity which is removed from the less strongly adsorbable gas which is taken off as product, or the more strongly adsorbable gas can be the desired product which is separated from the less strongly adsorbable gas. For example, it may be desired to remove impurities such as carbon monoxide and light hydrocarbons from a hydrogen-containing feed stream to produce a purified (99+%) hydrogen stream for use in a downstream catalytic process where these impurities could adversely affect the catalyst or the reaction. On the other hand, it may be desired to recover more strongly adsorbable gases, such as ethane, from a feedstream to produce an ethane-rich product.

In pressure swing adsorption, a multi-component gas stream is typically fed to at least one of a plurality of adsorption zones at an elevated pressure effective to adsorb at least one component, while at least one other component passes through. At a defined time, the feedstream to the adsorber is terminated and the adsorption zone is depressurized by one or more cocurrent depressurization steps wherein pressure is reduced to a defined level which permits the separated, less strongly adsorbed component or components remaining in the adsorption zone to be drawn off without significant concentration of the more strongly adsorbed components. Then, the adsorption zone is depressurized by a countercurrent depressurization step wherein the pressure on the adsorption zone is further reduced by withdrawing desorbed gas countercurrently to the direction of the feedstream. Finally, the adsorption zone is purged and repressurized. The combined gas stream produced during the countercurrent depressurization step and the purge step is typically referred to as the tail gas stream. The final stage of repressurization is typically performed by introducing a slipstream of product gas comprising the lightest gas component produced during the adsorption step. This final stage of repressurization is often referred to as product repressurzation.

In multi-zone systems there are typically additional steps, and those noted above may be done in stages. U.S. Pat. Nos. 3,176,444 issued to Kiyonaga, 3,986,849 issued to Fuderer et al., and 3,430,418 and 3,703,068 both issued to Wagner, among others, describe multi-zone, adiabatic pressure swing adsorption systems employing both cocurrent and countercurrent depressurization. The disclosures of these patents are incorporated by reference in their entireties.

Various classes of adsorbents are known to be suitable for use in PSA systems, the selection of which is dependent upon the feedstream components and other factors generally known to those skilled in the art. In general, suitable adsorbents include molecular sieves, silica gel, activated carbon, and activated alumina. When PSA processes are used to purify hydrogen-containing streams, the hydrogen is essentially not adsorbed on the adsorbent.

Improved processes are sought for the combination of pressure swings adsorption and reaction for reversible reactions.

Improved processes are sought for the isomerization of alkanes to form high octane products.

Processes are sought which extend the equlibrium conversion in providing a high octane product to proceed with a greater conversion per pass and with a high yield of a high octane product. In addition, processes are sought which substantially reduce the recycle of unreacted components.

SUMMARY OF THE INVENTION

Many commercial processes for the production of chemicals involve the integration of chemical reaction and separation—such as distillation, adsorption, and condensation, but not in the same zone. Conventionally, these reactions are carried out in the vapor phase at high pressure and the products of the reaction are separated at lower pressure by pressure swing adsorption techniques. For example, if the reaction involves the production of a readily-adsorbable product from at least one reactant which is non-adsorbable, the non-adsorbable reactant is separated at low pressure following the reaction and retered to the reactor. Generally the conversion of the reactant in the reactor is low, requiring large amounts of the reactant to be recompressed to the higher reaction pressure and returned to the reactor as a recycle gas. This recycle operation is costly in terms of capital and operating costs. When the reaction and the PSA process can be combined, the overall process can be improved considerably to improve the conversion of the reaction and to decrease the amount of recycle.

The purpose of this invention is to provide a process for the continuous isomerization of an alkane to produce an isomerized product through contacting the alkane with a pressure swing adsorption and reaction zone wherein a catalyst for isomerization and an adsorbent for the alkanes is integrated to improve the overall conversion and yield of high octane product. The alkane may be n-pentane and the isomerized product 2-methylbutane or 2,2-dimethylpropane, the alkane may have from 6 up to about 8 carbon atoms with no more than one methyl branch and the isomerized product having the same number of carbon atoms and at least two methyl branches, or the reactant may be a mixture of the foregoing alkanes with the corresponding isomerized products being formed. The advantage of the present invention over the conventional process is the higher octane of the product and that this higher octane can be achieved at lower severity since the product is removed from the reaction zone as soon as it is produced. The lower operating severity provides longer catalyst life, and reduces the amount of heavy paraffins lost to side reactions such as cracking.

In one embodiment, the present invention is a process for the isomerization of a $C_5/C_6$ hydrocarbon feed mixture. The $C_5/C_6$ hydrocarbon feed mixture comprises $C_5$ and $C_6$ normal paraffin components as reactants. The process produces a high octane product comprising mono and dimethyl branched paraffins. The process comprises the series of steps that follow. The feed mixture is passed at reaction conditions including a reactor temperature and a reactor pressure in the presence of hydrogen to carry out at least one reversible isomerization reaction in a fixed bed of a pressure swing adsorption and reaction zone. The fixed bed contains a physical mixture of a selective adsorbent and a catalyst. The selective adsorbent is selective for the adsorption of at least a portion of the mono methyl branched paraffins and the normal paraffins. The catalyst is selective for the isomerization of the feed mixture to produce mono and dimethyl branched paraffins. A first effluent stream comprising hydrogen and the high octane product is withdrawn. The fixed bed is countercurrently depressurized and a desorption effluent comprising normal paraffins is withdrawn. The fixed bed is repressurized with a repressurization stream comprising hydrogen. The above series of steps is repeated to provide a continuous process.

In another embodiment, the invention relates to a process for the isomerization of a $C_5/C_6$ hydrocarbon feed mixture. The feed mixture comprises normal paraffin components as reactants which, upon isomerization, will produce a high octane product comprising mono and dimethyl branched paraffins. The process comprises the series of steps that follow. The feed mixture at reaction conditions including a reactor temperature and a reactor pressure in the presence of hydrogen is passed to a fixed bed of a pressure swing adsorption and reaction zone to carry out at least one reversible reaction. The fixed bed contains a homogeneous mixture of a selective adsorbent and a catalyst. The selective adsorbent is selective for the adsorption of at least a portion of the mono methyl branched paraffins and the normal paraffins. The catalyst is selective for the isomerization of the feed mixtures to produce mono and dimethyl branched paraffins. The reactants are isomerized and a first effluent stream comprising hydrogen and the high octane product is withdrawn. The passing of the feed mixture to the fixed bed is terminated and the fixed bed is countercurrently purged with a first purge seen comprising normal pentane. The normal pentane produces additional isomerization of the normal paraffin components and a second effluent stream comprising mono methyl branched paraffins is withdrawn. The fixed bed is countercurrently depressurized to a desorption pressure and a desorption effluent stream comprising normal paraffins is withdrawn. The fixed bed is repressurized with a repressurization stream comprising hydrogen. The above steps are repeated to provide a continuous process.

DETAILED DESCRIPTION OF THE INVENTION

Figure 1:
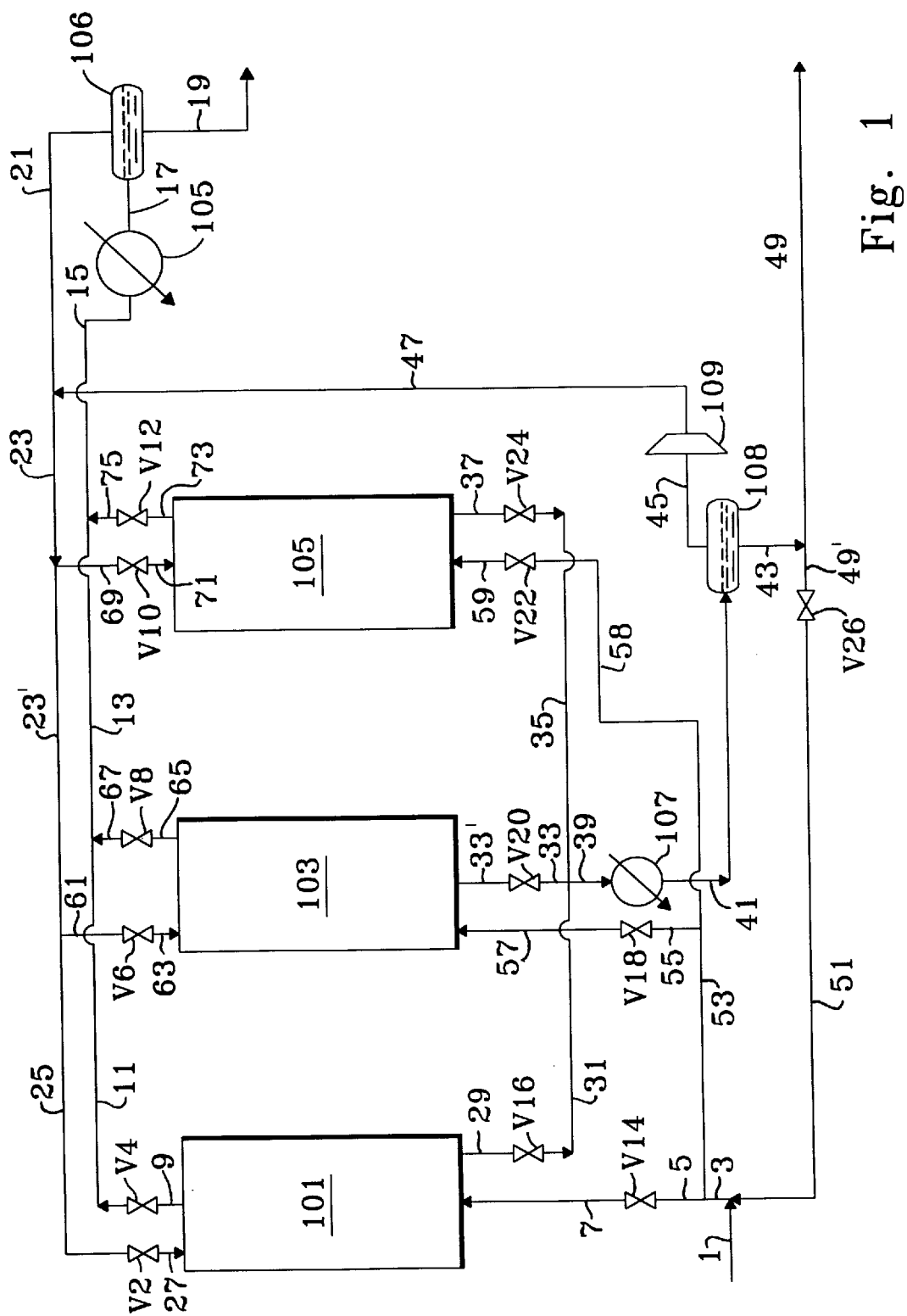
FIG. 1 is a schematic flow diagram of the process of the present invention for the production of a high octane product.

Typical light naphtha streams available in petroleum refineries are poor in highly branched paraffins such as 2,2 dimethyl butane and 2,3 dimethyl butane but rich in normal paraffins and mono-branched paraffins. The reactions to form the highly branched paraffins occur as below:

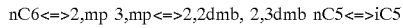

The present invention provides a process in which 2,mp and 3,mp and nC6 are retained in a catalyst bed and 2,2 dmb and 2,3 dmb are rejected which permits the reaction to be carried to completion. Similarly, it was found that when n-pentane was retained and iC5 was not retained as strongly, then the reaction of nC5 to iC5 can be carried substantially over equilibrium. This can be accomplished by using a bed containing a physical mixture of catalyst and adsorbent particles, the catalyst being either tungstated zirconia, sulfated zirconia or Pt/mordenite. The adsorbent can be such as Ca—Sr—X or Silicalite or Ferrierite. The adsorbent preferentially adsorbs normal and mono-branched paraffins over dimethyl paraffins.

Integration of the pressure swing adsorption separation process with a, reversible chemical reaction results in a combination of two unsteady-state phenomena. By the proper combination of catalyst, adsorbent, reaction and adsorption rates, and adsorbents having varying degrees of selectivity for the reactants and products, a processing cycle can be developed to improve the conversion of the reactants compared to a conventional steady-state reaction and separation system. Reversible reaction systems—particularly those systems wherein one reaction is favored at a high pressure, and the reverse reaction is favored at a lower pressure, and where one or more of the reactants may be more-readily or less-readily adsorbable than another—are particularly preferred systems for pressure swing adsorption and reaction processes. Such systems are more preferred if the rates of reaction are similar to the rate of adsorption and desorption of the reactants and products for the range of temperatures and pressures over which the process is operated. In a simple system a feedsteam comprising a non-adsorbable reactant is passed to a PSA reaction zone to produce a more-readily adsorbable product by reaction at high pressure. If an excess of reactant is present in the feedstream, an effluent stream comprising the non-adsorbable reactant will be withdrawn. Upon depressurization, the more-readily adsorbable product would be desorbed and withdrawn as a product stream. Most commercial processes are not this simple and often require at least a second, less-readily reactant adsorbable reactant to form the product of the reaction. In addition, there will be co-products, some of which will be non-adsorbable and some will be more-readily adsorbable. The non-adsorbable co-products will be withdrawn with the effluent during a reaction/adsorption step, while a more-readily adsorbable co-product will be recovered with the product and require further separation.

In a reaction system comprising both an adsorbent selective for the adsorption of the readily-adsorbed product and the more-readily adsorbed co-product, the equilibrium reversible reaction can be made to favor the production of the product by removing the product and the co-product from the reaction zone as soon as they are produced while the non-adsorbable reactant is withdrawn. When the reaction takes place in a fixed adsorbent bed, mass transfer zones of each species of less-readily, readily-, and more-readily adsorbable components are formed within the fixed bed. As the reaction proceeds during a reaction/adsorption step, the reactant mass transfer zones lead the product mass transfer zones. It was discovered that when one of the reactants is less-readily adsorbable, the conversion can be improved by the addition of a high pressure purge step following the adsorption/reaction step wherein the non-adsorbable reactant is employed to cocurrently purge the fixed bed. Surprisingly, it was discovered that when the reactant employed in the purge step also reacts to produce a less-readily adsorbable quantity may be withdrawn which further reduces the amount of recycle in the process. During the high pressure purge step, the less-readily adsorbable reactant is converted to product while the unreacted reactant continues to be withdrawn from the bed. This technique for purging at high pressure to drive the reaction toward completion may be applied to reactions wherein the co-product is recovered with the product on depressurization or wherein the co-product is non-adsorbable and is recovered with the intermediate effluent at high pressure.

During the adsorption/reaction step, the reaction may be exothermic and produce heat, or the reaction may be endothermic and consume heat. It is preferred to maintain the reaction temperature near isothermal conditions within the bed. Thus, provisions are made to add or remove heat from the bed as the reaction proceeds. Such provisions may include the use of heat exchange coils or tubes, or the use of a diluent such as nitrogen, methane, and mixtures thereof, in the reaction mixture to maintain the temperature change or the difference between the reaction and adsorption temperatures in the bed to less than 20° C., and preferably to maintain the temperature change in the bed to less than 15° C.

The bed may be depressurized in a countercurrent manner, i.e., in a direction opposite to the flow of the synthesis gas during the previous adsorption/reaction step. The desorption effluent is recovered from the feed end of the bed. The bed also may be depressurized in a cocurrent manner, i.e., in the same direction and the adsorption/reaction step, wherein the desorption effluent is withdrawn from the effluent end of the bed. The isomerization reaction requires the reaction to be carried out in the presence of hydrogen. Preferably, the molar ratio of hydrogen to hydrocarbon will be between about 10:1 and about 1:10 and more preferably, the ratio of hydrogen to hydrocarbon will range from about 3:1 to about 1:3. Preferably, the reaction and adsorption conditions in the pressure swing adsorption and reaction zone will range from a reaction temperature from about 150° C. to about 250° C., and more preferably will range from about 150° C. to about 225° C. The reaction may be carried out over a wide range of pressure which retains the reactants and products in the vapor state, preferably, the reaction pressure will range from about 450 kPa to about 1150 kPa.

A wide variety of solid catalysts and adsorbents are available, and each isomerization application may require a different combination of solids. The solid or mixture of solids acting as a catalyst may be any of the commonly used isomerization catalysts including, but not limited to, platinum on mordenite, aluminum chloride on alumina, and platinum on sulfated or tungstated metal oxides such as zirconia. See generally, Kirk-Othmer *Encyclopedia of Chemical Technology*, 3rd ed.; Grayson, M., Eckroth, D., Eds.; John Wiley & Sons: New York, Vol. 11 p.664, Vol 12 pp. 911 and 922, and Vol 15 p. 651. Depending upon the composition of the feed, several different catalysts may be combined in order to accomplish the catalysis function. The preferred catalyst is platinum on tungstated zirconia, see, for example, WO 95/03121, U.S. Pat. No. 5,113,034, U.S. Pat. No. 5,422,327, U.S. Pat. No. 4,663,304, U.S. Pat. No. 5,489,733 and U.S. Pat. No. 5,420,092. The most preferred catalyst contains from about 7.5 to about 12.5 weight percent tungstate on zirconia with from about 0.25 to about 0.5 weight percent platinum.

The adsorbent solid or mixture of solids are selected to either have a pore size capable of admitting alkane reactants but not the isomerized products, or an affinity for alkanes with no or low branching. Examples of suitable adsorbents include, but are not limited to, silicalite, ferrierite, Ca-A zeolite, MAPO-31, SAPO-31, SAPO-11, EU-1, ZSM-12, SAPO-5, Y-82 faujasite, Erionite, zeolite beta exchanged with sodium, lithium, potassium, barium, calcium, strontium or combinations thereof, faujasite such as X zeolite exchanged with calcium and strontium, mordenite exchanged with sodium, lithium, potassium, barium, calcium, strontium, or combinations thereof. Depending upon the composition of the feed, several different adsorbents may be combined in order to accomplish the separation function. For example, when the feed contains $C_6$ to $C_8$ almanes, a portion of the adsorbent should retain both normal and mono-methyl-branched alkanes, so that they are retained in the bed until they are isomerized to form multi-methyl-branched isomerized products. Preferred adsorbents capable of retaining both normal and mono-methyl-branched alkanes are silicalite and X zeolite exchanged with calcium and strontium. When the feed contains n-butane or n-pentane, a portion of the adsorbent should retain only normal alkales, since the $C_4$ and $C_5$ mono-methyl-branched alkanes are isomerized products which are collected.

A preferred adsorbent capable of retaining only normal alkanes is Ca-A zeolite. The adsorbents may be combined in different volume ratios depending upon the composition of the feed. As an illustration, in an embodiment where the adsorbent is a mixture of Ca-A zeolite and another adsorbent and the feed contains n-butane or n-pentane, the greater the concentration of n-butane or n-pentane present in the feed increases, the greater the required concentration of Ca-A zeolite in the adsorbent mixture, or in an embodiment where the adsorbent is a mixture of X zeolite exchanged with calcium and strontium and another adsorbent and the feed contains $C_6$ to $C_8$ alkanes, the greater the concentration of $C_6$ to $C_8$ alkanes present in the feed, the greater required the concentration of X zeolite exchanged with calcium and strontium in the adsorbent mixture.

The feed introduced to the pressure swing adsorption and reaction system contains at least one alkane which is to undergo catalytic isomerization to form at least one isomerized product. Examples of suitable alkanes include: normal pentane, 2-methylbutane, normal hexane, 2-methylpentane, 3-methylpentane. Preferably the feed contains normal pentane, normal hexane, 2-methylpentane, and 3-methylpentane. The feed is usually derived from other refinery processes and may contain cyclic alkanes, olefinic hydrocarbons, aromatic hydrocarbons, and other hydrocarbons. The feed may also be the effluent of a fixed bed isomerization unit where alkane reactants and the corresponding isomerized products are present in amounts determined by the conversion in the fixed bed which is limited by thermodynamic equilibrium. The liquid hourly space velocity of the feedstream is typically from about 0.05 to about 5.

Examples of the isomerized products include: 2-methylpropane, 2-methylbutane, 2,2-dimethylpropane, 2,3-dimethylbutane, 2,2-dimethylbutane, 2,2-dimethylpentane, 3,3-dimethylpentane, 2,3-dimethylpentane, 2,4-dimethylpentane, 2,2,3-trimethylbutane, 2,2-dimethylhexane, 3,3-dimethylhexane, 2,3-dimethylhexane, 3,4-dimethylhexane,2,4-dimethylhexane,2,5-dimethylhexane,2,2,3-trimethylpentane, 2,3,3-trimethylpentane, 2,3,4-trimethylpentane, and 2,2,4-trimethylpentane. Preferably the high octane product of the present invention for the isomerization of C5/C6 paraffin hydrocarbons comprises mono methyl branched paraffins, such as 2-methylpentane and 3-methylpentane, and dimethyl branched paraffins such as 2,2-dimethyl butane and 2,3-dimethyl butane. The octane quality of the high octane product of the present invention will range from about 90 to about 105 research octane, and when the process is operated to produce an intermediate product, the octane of this second effluent stream ranges from about 74 to about 93 research octane.

Operating conditions will depend upon the catalyst and adsorbent selected. Preferred operating temperatures for the process are about 100° C. to about 500° C., most preferably the operating temperature will range from about 150° to about 250° C. Preferably the reaction pressure ranges from about 4 kPa to about 2100 kPa, and most preferably the reaction pressure ranges between about 450 kPa (65 psia) and about 1500 kPa (200 psia). Preferably the desorption pressure ranges between about 70 kPa, (10 psia) and about 360 kPa (45 psia), and more preferably the desorption pressure ranges between about atmospheric pressure and about 360 kPa (45 psia). As outlined above, the process conditions are set so that all the streams are in the gas phase.

Without intending any limitation on the scope of the present invention and as merely illustrative, this invention is explained below in specific terms as applied to one specific embodiment of the invention, the continuous isomerization of normal pentane and n-hexane, 2-methylpentane, and 3-methylpentane to form 2,2-dimethylbutane and 2,3-dimethylbutane using a mixture of X zeolite exchanged with one or more alkaline earth metals such as calcium and strontium, and platinum on tungstated zirconia in a 4:5 volume ratio to effect catalysis of the isomerization and the separation of the products and reactants through adsorption. Preferably, the fixed bed pressure swing adsorption and reaction zone of the present invention contains a physical mixture of the catalyst and the adsorbent. More preferably, the fixed bed pressure swing adsorption and reaction zone of the present invention contains a homogeneous mixture of catalyst and adsorbent. The catalyst and adsorbent may be present as separate particles, or the adsorbent and catalyst may be combined into a single particle comprising both the catalyst and adsorbent. The single particle may comprise layers of catalyst and adsorbent such as layered particle having a core of adsorbent and an outer layer of catalyst.

The pressure swing adsorption process is an essentially adiabatic process for separating a multi-component fluid containing at least one selectively adsorbable component. The PSA process of the invention relates to conventional PSA processing in which each bed of an adsorption zone undergoes, on a cyclic basis, high pressure adsorption, optional cocurrent depressurization to intermediate pressure level(s) with release of void space gas from the effluent end of the bed, depressurization to lower desorption pressure with the release of desorbed gas from the feed end of the bed, with or without purge of the bed, and repressurization to higher adsorption pressure. The adsorption zone is then countercurrently or cocurrently depresserzed to a desorption pressure that is at or above atmospheric pressure with the more adsorbable component(s) being discharged from the feed end thereof as a product. In the multi-bed adsorption systems to which the invention is directed, the displacement or purge gas used for each bed is obtained by diverting a portion of the gas released from that or another bed in the system during the adsorption steps. Repressurization of the bed is obtained by introducing a portion of the purge gas or by introducing the synthesis gas at the adsorption pressure.

Those skilled in the art will appreciate that the high pressure adsorption step of the PSA process comprises introducing the PSA feedstream to the feed end of the adsorbent bed at a high adsorption pressure. The less readily adsorbable component(s) passes through the bed and is discharged from the effluent or produce end thereof. Adsorption fronts comprising the more adsorbable component(s) are established in the bed with the fronts likewise moving through the bed from the feed end toward the product end thereof. When the feedstream contains a less readily adsorbable component and a more readily adsorbable component, a leading adsorption front of the more readily adsorbable component will be established and will move through the bed in the direction of the product or discharge end thereof.

DETAILED DESCRIPTION OF THE DRAWINGS

Figure 2:
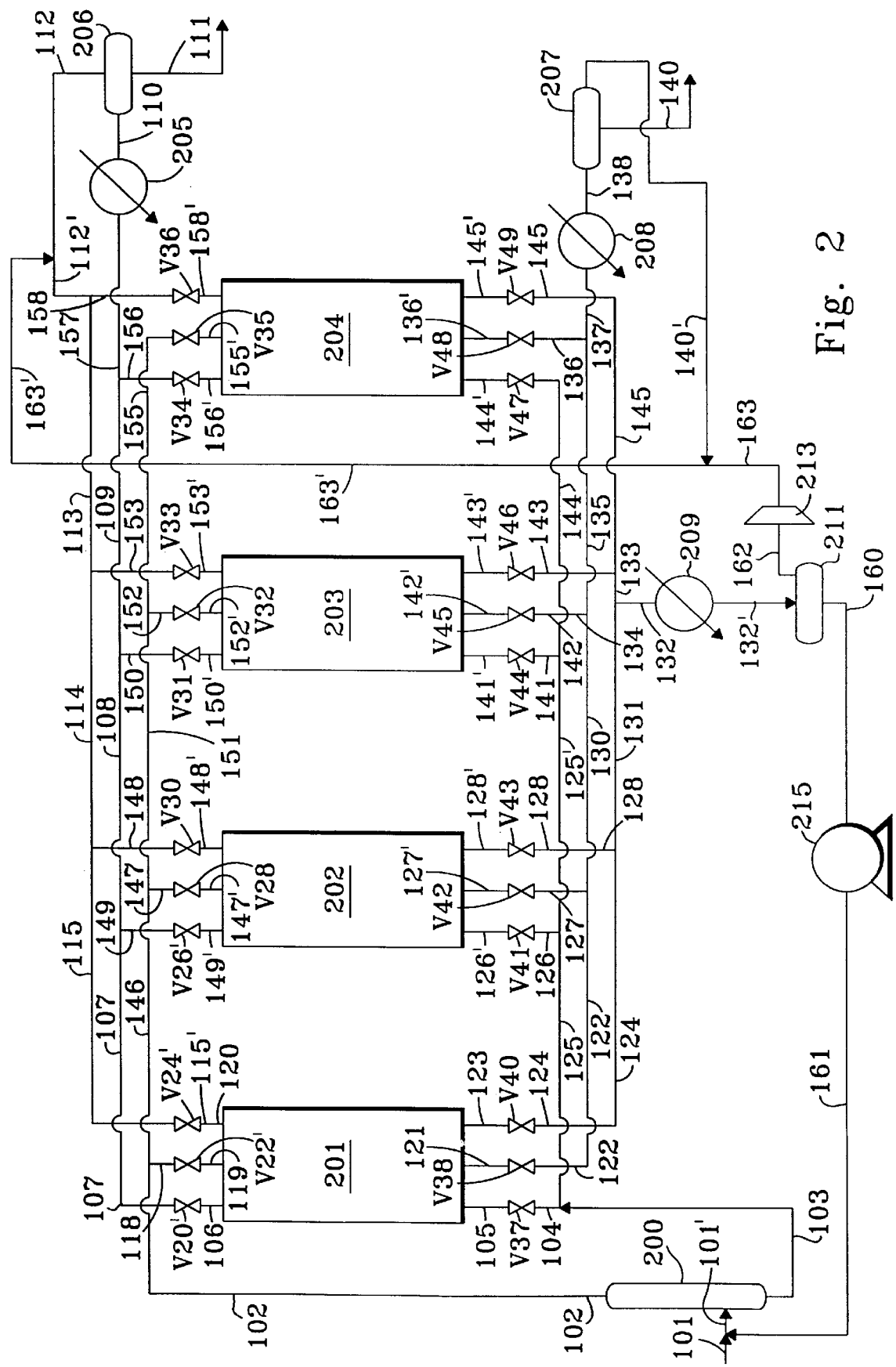
FIG. 2 is a schematic flow diagram of the process of the present invention employing a high pressure invention employing a high pressure, countercurrent purge step.

The further description of the process of this invention is presented with reference to the attached schematics, FIG. 1 and FIG. 2. The figures represent preferred arrangements of the invention and are not intended to be a limitation on the generally broad scope of the invention as set forth in the claims. Of necessity, some miscellaneous appurtenances including valves, pumps, separators, heat exchangers, etc. have been eliminated. Only those vessels and lines necessary for complete and clear understanding of the process of the present invention are illustrated.

Referring to FIG. 1, a schematic diagram of a process flow diagram of the present invention is illustrated. The operation of the pressure swing adsorption and reaction process illustrated in FIG. 1 can be employed on a continuous or periodic operation. For continuous operation, at least 3 fixed beds are preferred to provide a continuous flow of high octane product and intermediate octane product. A $C_5/C_6$ hydrocarbon feed mixture is passed in line 1 to lines 3 and 5, valve V14 and line 7 to the feed end of a pressure swing adsorption with reaction (PSAR) vessel 101 which contains a homogeneous mixture of a selective adsorbent and an isomerization catalyst. The $C_5/C_6$ hydrocarbon feed mixture is passed to the PSAR vessel 101 at a reaction temperature and a reaction pressure. Initially the PSAR vessel may be preloaded with hydrogen at the reaction pressure or hydrogen may be introduced with the feed mixture. As the feed mixture enters the PSAR vessel, the isomerization reaction proceeds. The normal $C_6$ paraffins first react to produce methylcyclopentanes which react further to produce dimethyl butanes. The hydrogen and the dimethyl butanes which are non-adsorbable are recovered in a first effluent stream 9 which exits the PSAR vessel 101 via line 9, valve V4, and lines 11, 13, and 15 to a first condenser 105 and via line 17 to a first separator 106. The first effluent stream 15 is cooled in condenser 105 to at least partially condense a first hydrocarbon phase which is recovered as a high octane product in line 19. A high pressure vent stream, comprising hydrogen is recovered from the first separator 106 in line 21. The passing of the feed mixture 7 to the PSAR vessel 101 is continued until a point prior to the breakthrough of methylcyclopentane and normal hexane. At this point, the feed mixture flow to the PSAR vessel 101 is terminated and the PSAR vessel 101 is countercurrently depressurized to a desorption pressure to produce a desorption effluent 29. The desorption effluent is passed via line 29, valve V16, line 31, and line 39 to a second condenser 107 which cools the desorption effluent to provide a cooled desorption effluent 41 and the cooled desorption effluent is passed via line 41 to a second separator 108. In the second separator 108, a second vent stream 45 comprising hydrogen at desorption pressure and an intermediate octane stream 43 are produced. At least a portion of the intermediate octane stream 43 is reed via line 49', valve V26 and line 51 to be admixed with the feed mixture 1 to improve the overall conversion. A portion of the intermediate octane stream which comprises methylpentanes and normal hexane may be recovered as an intermediate octane product in line 49. The second vent stream 45 may be recompressed in compressor 109 to provide a compressed vent stream 47 at the reaction pressure and the compressed vent stream 47 may be combined with the high pressure vent stream 21 to produce a hydrogen purge stream 23'. At the completion of the countercurrent depressurization step, the PSAR vessel 101 is repressurized by introducing the hydrogen purge stream 23' via line 23, line 23', line 25, valve V2 and line 27. The above steps of reaction with adsorption, countercurrent depressurization, and repressurization are repeated for PSAR vessel 101.

The process illustrated in FIG. 1 is operated in a continuous fashion by alternating the operation of PSAR vessels 101, 103, and 105 in a cyclic manner to provide a continuous flow of product streams from the process. For example, when PSAR vessel 101 is switched from the reaction/adsorption step to the countercurrent depressurization step, the feed mixture is passed to PSAR vessel 103 via lines 1, 3, and 53, valve V18 and line 57. The first effluent is removed from PSAR vessel 103 via line 65, valve V8, line 67, line 13, and line 15 to the first condenser 105 and the first separator 106 for recovery of the high octane product. During the countercurrent depressurization step, the desorption effluent from PSAR vessel 103 is passed through line 33', valve V20, line 33, and line 39 to the second condenser 107 and via line 41 to the second separator 108. During the repressurization step, the hydrogen purge stream 23' is passed to PSAR vessel 103 via line 23', line 23, line 61, valve V6, and line 63. Similarly, PSAR vessel 105 in the reaction/adsorption step is charged with the feed mixture 1 via line 53, line 58, valve V22, and line 59. The first effluent stream is withdrawn from PSAR vessel 105 via line 73, valve V12, line 75 to line 15 for high octane product recovery from separator 106. During the countercurrent desorption step, the desorption effluent is withdrawn in line 37 and is passed to valve V24, line 35, and line 39 to intermediate product recovery. During repressurization PSAR vessel 105 is repressurized by passing the hydrogen purge stream 23' via line 69, valve V10, and line 71 to PSAR vessel 105.

Referring to FIG. 2, a $C_5/C_6$ hydrocarbon feedstream 101 is admixed with a recycle stream 161 and a combined feedstream 101' is passed to a splitter zone 200. Splitter zone 200 which employs conventional fractionation to split the combined feedstream into a light feedstream 102 comprising normal pentane and a heavy feedstream 103 comprising normal hexane. Preferably, the light feedsteam comprises greater than about 60% normal pentane, and more preferably, the light feedsteam comprises more than about 80% normal pentane, and most preferably, the light feed stream comprises more than about 90% normal pentane. In a reaction/adsorption step, the heavy feedstream 103 is passed at a reaction temperature and a reaction pressure as a vapor via lines 103 and 104, valve V37 and line 105 to PSAR vessel 201 to produce a first effluent stream 106 which is passed via valve V20', line 107, line 108, line 109, and line 157 to a first condenser 205 to provide a cooled effluent stream 110. The cooled effluent stream 110 is passed to a first separator 206 to provide a first vent stream 112 comprising hydrogen and a high octane product stream 111 comprising dimethyl butanes. The passing of the heavy feedstream to PSAR vessel 201 is terminated prior to the breakthrough of normal hexane and the PSAR vessel 201 is first purged in a first purge step at the reaction pressure with a portion of the light feedstream 102 which is introduced via line 102, line 118, valve V22' and line 119 and a purge effluent stream 121 comprising isopentane and methylpentanes is withdrawn. As the normal pentane in the light feedstream is introduced to the PSAR vessel 201, it is believed that the normal pentane displaces the adsorbed normal hexane and as these normal pentane proceeds further, a portion of the normal pentane is converted to isopentane. Because the isopentane is a weaker desorbent than normal pentane, the isopentane now displaces mostly the methylpentanes and not as much of the normal hexane thereby producing a high pressure purge effluent comprising isopentane and methylpentanes. The high pressure purge step is terminated prior to the breakthrough of normal pentane. The high pressure purge effluent is withdrawn in line 121 and passed via valve V38, line 122, line 130, line 135, and line 137 to a second condenser 208 to provide a condensed high pressure purge effluent 138. The condensed high pressure purge effluent 138 is passed to a second separator 207 to provide an intermediate product 140 and a second vent stream 140' comprising hydrogen. The second vent stream 140' is combined with the first vent stream 112 via line 140' and line 163'. At the completion of the first purge step with normal pentane, the PSAR vessel 201 is countercurrently depressurized to produce a low pressure purge effluent stream 123 which is passed via lie 123, valve V40, line 124, line 131, and line 132 to the third condenser 209 to provide a condensed low pressure purge effluent 132'. The condensed low pressure purge effluent 132' is passed to a third separator 211 to provide a third vent stream 162 and a heavy hydrocarbon stream 160. At least a portion of the heavy hydrocarbon same 160 comprising normal hexane is passed to pump 215 to return the portion of the heavy hydrocarbon stream to be admixed with the feedstream 101 as the recycle stream. At the completion of the countercurrent depressurization step, the PSAR vessel 201 is returned to the reaction pressure by repressurization with the combined vent stream 112' comprising hydrogen. Although this repressurization can be carried out in a cocurrent or countercurrent fashion, it is preferred to repressurize in a countercurrent direction to move any remaining normal paraffins in the PSAR vessel 201 toward the feed end of the vessel prior to the reintroduction of the feedsteam. The process comprising the steps of reaction/adsorption, high pressure purging, depressurization, and repressurization is repeated for PSAR vessels 201, 202, 203, and 204 on a cyclic basis to provide a continuous process. Each of the above steps is implemented sequentially for each of the above 4 PSAR vessels to provide a continuous flow of high octane and intermediate products.

As illustrated above with respect to PSAR 201, each of the remaining 3 PSAR vessels cycles through the steps of the process. For example, PSAR vessel 202 in the reaction/adsorption step is charged with the heavy fee am 103 via line 125, line 126, valve V41, and line 126'. The first effluent stream is withdrawn in line 149' and passed to valve V26', line 149, line 108, line 109, and line 157 to recover the high octane product 111 and the first vent stream 112. During the first purge, or high pressure purge step, the light feedstream 102 is passed to PSAR vessel 202 via line 102, line 146, line 147, valve V28 and line 147'. The high pressure purge effluent stream is withdrawn from PSAR vessel 202 in line 127', valve V42, line 127, line 130, line 135, and line 137 to intermediate product recovery from separator 207. During the countercurrent depressurization step, the desorption effluent 128' is passed via line 128', valve 143, line 128, line 131, and line 132 to the third condenser 209 and separator 211 for the recovery of the heavy hydrocarbon stream 160. In the repressurization mode, the combined vent gas stream 112' is passed to the PSAR vessel 202 via lines 113, 114, and 148, valve V30 and line 148'.

Similarly, for the operation of the operation of the process with respect to PSAR vessel 203, the heavy feedstream is introduced during the reaction/adsorption step via line 103, line 125, line 125', line 141, valve V44 and line 141' and the first effluent stream is withdrawn via line 150', valve V31, line 150, line 109, and line 157 to the recovery of the high octane product 111. In the high pressure purge step, the light feedstream 102 is passed via line 102, line 146, line 151, line 152 and line 152' and the high pressure purge effluent stream is withdrawn in line 142' and passed to intermediate product recovery via valve V45, line 134, line 135, and line 137. When PSAR vessel 203 is countercurrently depressurized, the desorption effluent is withdrawn via line 143', valve V46, line 143, line 133, and line 132 for the recovery and recycle of the heavy hydrocarbon stream comprising normal paraffins such as normal hexane. PSAR vessel 203 is repressurized by passing the combined vent gas stream 112' to line 113, line 153, valve V33, and line 153'.

The operation of the process with respect to PSAR vessel 204 is similar to that of PSAR vessel 203. During the reaction/adsorption step, the heavy feedstream 103 is passed via lines 125, 125', and 144, valve V47 and line 144' and the first effluent stream is withdrawn to high octane product recovery via line 156', valve V34, line 156 and line 157. During the high pressure purge step, the light feedstream 102 is introduced via lines 102, 146, 151, and 155, valve V35 and line 155', and the high pressure purge effluent is withdrawn to intermediate product recovery via line 136', valve V48, line 136, and line 137. During the countercurrent depressurization step, the desorption effluent is withdrawn and passed to the recovery of the heavy hydrocarbon stream 160 via line 145', valve V49, line 145 and line 132. During the repressurization step, the combined vent gas stream 112' is passed to the PSAR vessel 204 via line 158, valve V36, and line 158'. The PSAR vessels may be cycled in any order with each PSAR vessel in a different mode of the process. It is preferred that initially at least one of PSAR vessels be pressurized to a reaction pressure with a hydrogen-containing gas.

It will further be understood that various changes and modifications can be made in the details of the PSA zone as herein described and illustrated above without departing from the scope of the invention as set forth in the appended claims. In addition the number of beds employed may be varied depending upon the circumstances and results desired in any given application. Accordingly, the individuals PSA steps described, as well as conventional variations thereof, are generally known by those skilled in the art and need not be further described herein. It will be further understood that PSA systems necessarily incorporate various conduits, valves, and other control features to accomplish the necessary switching of adsorbent beds from one step to the next, in appropriate sequence as in conventional PSA operations.

The following examples are provided to illustrate the present invention and are not intended to limit the scope of the claims that follow.

EXAMPLES

Example I

A series of adsorption screening tests for the reactants, intermediate products, and final products of the $C_5/C_6$ isomerization reactions. These tests were carried out in a modified BEI adsorption apparatus. The apparatus measures adsorption by sensing changes in pressure and temperature inside a reference volume which is attached to an adsorption vessel containing the adsorbent sample. The adsorbent sample was maintained at a steady temperature by the action of a temperature controlled heated chamber. The reference volume can be isolated from the adsorbent vessel by means of an isolation valve. The reference volume may also be connected or isolated from a vapor source by means of another isolation valve, and finally the absolute pressure of the reference volume may be controlled by means of a high vacuum pump which is also connected to the reference volume by means of a third isolation valve. Adsorption measurements were made by first evacuating the reference volume and the adsorbent sample vessel to a pressure of approximately $5 \times 10^{-6}$ torr while heating the adsorbent and adsorbent vessel to an activation temperature of approximately 300° C. The temperature of activation was controlled and monitored. After the adsorbent sample has been dried at 300° C. for 4 hours, its volume and weight are measured and it is loaded in the sample chamber. Vacuum is applied to the system at 250° C. for several hours until no increase in pressure is detected. At this time, the temperature was adjusted to 225° C. for collection of isotherm data. After activation, the sample was isolated from the reference volume. The reference volume also evacuated to $5 \times 10^{-6}$ torr was also isolated from the vacuum pump and was charged to a vapor pressure of about 5 torr with purge sample hydrocarbon vapor. The pressure of the sample hydrocarbon vapor was monitored by a pressure transducer. Once stable readings were obtained on both the pressure and temperature within the reference volume, the isolation valve separating the adsorbent sample from the reference volume was opened and the pressure and temperature of the system were monitored until they stabilized, i.e., changing no more than by 1 part in $10^6$ within one minute. Adsorption isotherms were obtained by repeating the isolation, charging and equilibration of the reference volume with the adsorbent vessel until a pre-determined loading level or pressure level were obtained. Adsorbent loadings of each of the following hydrocarbons: a) normal pentane, b) isopentane, c) normal hexane, d) 2-methylpentane, and e) 2,2-dimethyl butane on silicalite were determined.

Figure 3:
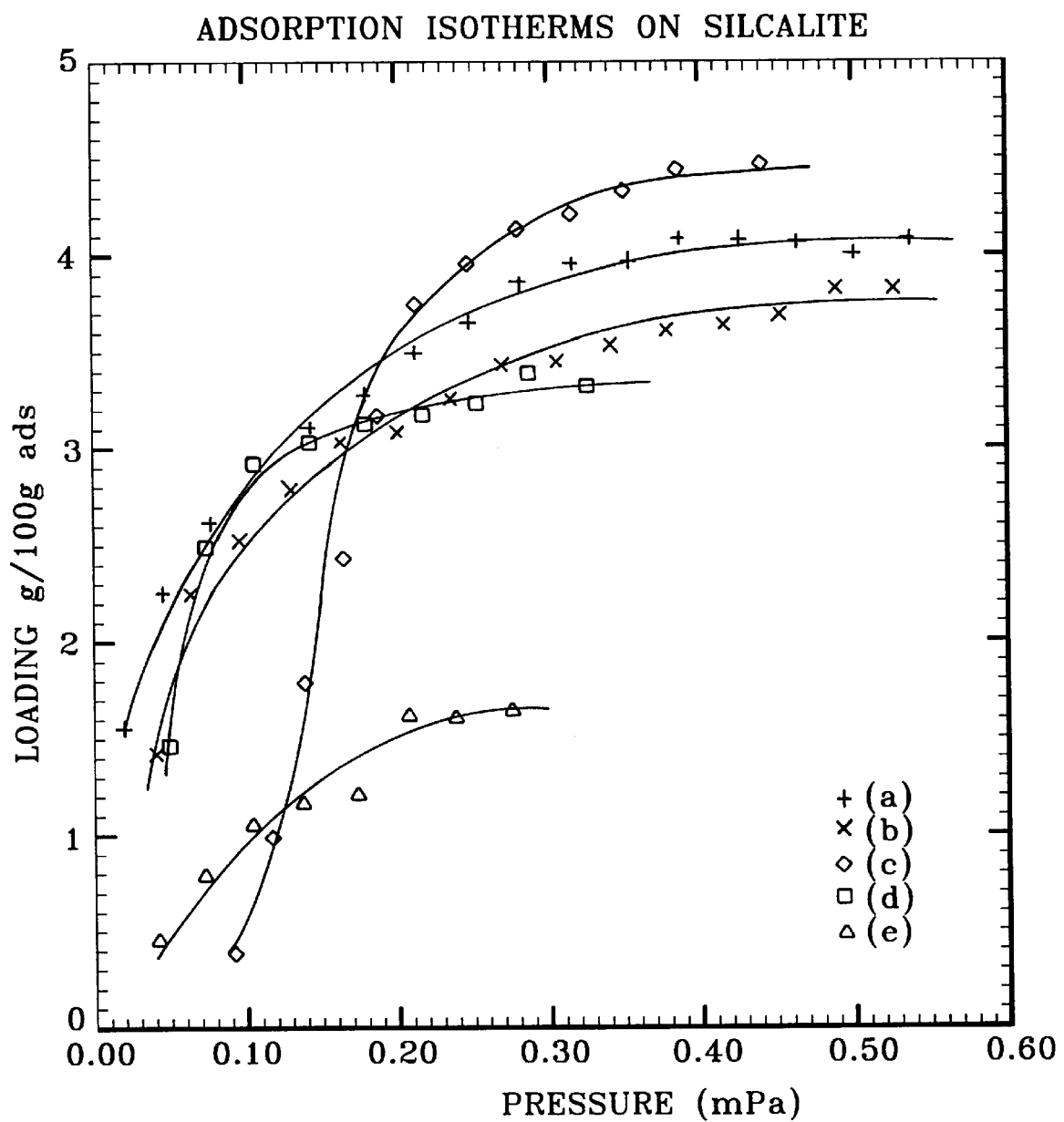
FIG. 3 is an adsorbent isotherm chart showing the relative loadings of isomerization reactants and products at a reaction temperature.

The adsorption isotherms at 225° C. over silicalite adsorbent for the above list of hydrocarbons is shown in FIG. 3. From the loadings shown in the range of about 30 psia to about 60 psia, the 2,2-dimethyl butane exhibited the lowest loading; the 2-methyl pentane showed an intermediate loading and the normal pentane showed the highest loading. All loadings were expressed in grams per 100 grams of adsorbent. These results support the conclusion that at reaction conditions, the highest octane materials (e) and (d) are least adsorbable, while the normal $C_5$ and $C_6$ hydrocarbons, the primary reactants, are most adsorbable. In all cases, the silicalite adsorbs normal and monomethyl paraffins over dimethyl paraffins. Thus, it is possible to retain the reactants and the intermediate products in a catalyst bed of a pressure swing adsorption and reaction system while rejecting the highest octane product. In this manner, the reaction can be carried to completion. Furthermore, the data suggest that the reaction of normal pentane to isopentane can also be carried out beyond equilibrium.

Example II

Isomerization reactions were carried out in a stainless steal tubular reactor approximately 45 cm in length and having an inside diameter of about 8 mm. The reactor was loaded with about 17 grams of a platinum-mordenite catalyst bound with alumina. Normal hexane (99% pure) was charged, at a liquid hourly space velocity of about 1 and at a rate of about 20 ml/hour, to the reactor which was maintained a temperature of 225° C. Hydrogen (99.9% pure) was passed to the reactor such that the hydrogen to hydrocarbon ratio was about 1. The reaction was carried out at two reaction pressures: 450 kPa (65 psia) and about 1150 kPa (165 psia). The results as shown in Table 1. The conversion and the production of higher octane products favored the lower pressure operation.

TABLE 1

NORMAL HEXANE ISOMERIZATION

| COMPONENT | PRESSURE | |
|---|---|---|
| | 450 kPa | 1150 kPa |
| 2,2-dimethyl butane | 18.09 | 15.06 |
| 2,3-dimethyl butane | 9.59 | 9.76 |
| 2-methylpentane | 33.34 | 34.31 |
| 3-methylpentane | 21.26 | 21.71 |
| normal hexane | 17.10 | 18.91 |
| Conversion, % | 82.9 | 81.1 |

Example III

The performance of an isomerization process for the conversion of a $C_5/C_6$ paraffin feedstock in a conventionally integrated reaction and adsorption process is best characterized by the Total Isomerization Process disclosed in U.S. Pat. No. 4,210,771. In such a process the octane of the product produced will be about 87 research octane and have an overall recovery of about 97 percent. In comparison, the process of the present invention will produce a high octane product having a research octane of about 92 with about the same overall recovery. The advantage of the present invention over the conventional process is the higher octane of the product and that this higher octane can be achieved at lower severity since the product is removed from the reaction zone as soon as it is produced. The lower operating severity provides longer catalyst life, and reduces the amount of heavy paraffins lost to side reactions such as cracking.

We claim:

1. A process for the isomerization of a $C_5/C_6$ hydrocarbon feed mixture comprising $C_5/C_6$ normal paraffin components as reactants to produce a high octane product comprising mono and dimethyl branched paraffins, said process comprising the following steps:

a) passing said feed mixture at reaction conditions including a reactor temperature and a reactor pressure in the presence of hydrogen to a fixed bed of a pressure swing adsorption and reaction zone to carry out at least one reversible reaction, said fixed bed containing a homogeneous mixture of a selective adsorbent for the adsorption of at least a portion of said mono methyl branched paraffins and said normal paraffins, and a catalyst selective for the isomerization of said feed mixture to produce said mono and dimethyl branched paraffins, isomerizing said reactants and withdrawing a first effluent stream comprising hydrogen and said high octane product;

b) terminating the passing of said feed mixture to said fixed bed and countercurrently purging said fixed bed with a first purge stream comprising normal pentane to produce additional isomerization of said normal paraffin components and withdrawing a second effluent stream comprising mono methyl branched paraffins;

c) countercurrently depressurizing said fixed bed to adsorption pressure and withdrawing a desorption effluent stream comprising said normal paraffins;

d) repressurizing said fixed bed with a repressurization stream comprising hydrogen, and e) repeating steps (a) to (d) to provide a continuous process.

2. The process of claim 1 wherein said repressurization stream comprises at least a portion of said first effluent stream.

3. The process of claim 1 wherein at least a portion of said first purge stream further reacts to form a mono branched paraffin.

4. The process of claim 1 further comprising condensing and separating said first effluent stream to provide separation of said repressurization stream and said product stream comprising dimethyl branched paraffins.

5. The process of claim 1 further comprising recycling at least a portion of said desorption effluent stream and damming said portion of the desorption effluent with the feed mixture prior to passing the feed mixture to the reactor.

6. The process of claim 1 wherein said reaction temperature ranges from about 150° C. to about 250° C.

7. The process of claim 1 wherein said reactor pressure ranges from about 450 kPa (65 psia) to about 1500 kPa (200 psia).

8. The process of claim 1 wherein the catalyst is selected from the group consisting of tungstated zirconia, aluminum chloride on alumina, sulfated zirconia, and platinum on mordenite.

9. The process of claim 1 wherein the selective adsorbent is selected from the group consisting of silicalite, ferrierite, and a metal exchanged faujasite.

10. The process of claim 9 wherein the metal exchanged faujasitt comprises an X zeolite exchanged with one or more alkaline earth metals.

11. The process of claim 1 further comprising separating a portion of said feed mixture to provide a light feed stream comprising normal pentane and passing a portion of said light feed stream to said fixed bed as said first purge stream.

12. The process of claim 11 wherein said light feed stream comprises more than about 80 precent normal pentane.

13. The process of claim 1 wherein said mono methyl branched paraffins comprise 2-methylpentane and 3-methyl pentane.

14. The process of claim 1 wherein said dimethyl branched paraffins comprise 2,2-dimethyl butane and 2,3-dimethyl butane.

15. The process of claim 1 wherein said second effluent stream comprises a research octane number ranging between 74 and 93.

16. The process of claim 1 wherein said high octane product comprises an octane number between about 90 and about 105.

17. The process of claim 1 further comprising admixing at least a portion of said desorption effluent with said feed mixture prior to said passing.

18. The process of claim 1 wherein said selective adsorbent and said catalyst are combined into a single particle having an outer layer comprising said catalyst.

* * * * *

UNITED STATES PATENT AND TRADEMARK OFFICE
CERTIFICATE OF CORRECTION

PATENT NO: 5,811,630

DATED: September 22, 1998

INVENTOR(S): HEMANT W. DANDEKAR and GREGORY A. FUNK

It is certified that error appears in the above-identified patent and that said Letters Patent is hereby corrected as shown below:

Claim 5, lines 6-7, "and damming said portion" should read - - and admixing said portion - -.

Signed and Sealed this

Fifteenth Day of December, 1998

Attest:

BRUCE LEHMAN

*Attesting Officer*    *Commissioner of Patents and Trademarks*